United States Patent
Swisher

(10) Patent No.: US 6,183,453 B1
(45) Date of Patent: Feb. 6, 2001

(54) BLOOD EVACUATION CONTAINER WITH BLOOD SPIKE NESTING FEATURE

(75) Inventor: David Rork Swisher, St. Charles, MO (US)

(73) Assignee: Sherwood Services, AG, Schaffhausen (CH)

(*) Notice: Under 35 U.S.C. 154(b), the term of this patent shall be extended for 0 days.

(21) Appl. No.: 09/196,414

(22) Filed: Nov. 19, 1998

(51) Int. Cl.7 .................................................. A61M 1/00
(52) U.S. Cl. ............................................................ 604/319
(58) Field of Search .................................. 604/118, 119, 604/317, 319, 320, 321, 415

(56) References Cited

U.S. PATENT DOCUMENTS

| | | | |
|---|---|---|---|
| 4,522,623 | 6/1985 | Laüterjüng | 604/319 |
| 4,957,492 | 9/1990 | McVay | 604/319 |
| 5,356,406 | 10/1994 | Schraga | 604/415 |
| 5,372,593 | 12/1994 | Boehringer et al. | 609/319 |
| 5,549,585 | 8/1996 | Maher et al. | 604/317 |
| 5,876,387 * | 3/1999 | Killian et al. | 604/319 |
| 5,944,703 * | 8/1999 | Dixon et al. | 604/319 |

\* cited by examiner

Primary Examiner—John G. Weiss
Assistant Examiner—David J. Cho

(74) Attorney, Agent, or Firm—Mark S. Leonardo; Brown, Rudnick, Freed & Gesmer, P.C.

(57) ABSTRACT

The invention relates to an apparatus and method for a one-handed procedure that encapsulates the connector of a blood evacuation system prior to reinfusion. The blood evacuation system comprises a separable, flexible inner bag inside an outer rigid container for reinfusing shed blood drawn from the collection chamber of a chest drainage unit. The outer rigid container includes a suction port connected to a source of vacuum for applying a negative pressure within the interstitial space between the rigid container and the inner flexible bag which causes blood to be drawn into the bag. Once the bag is filled to a desired level, it is removed from the container and suspended using a suitable suspension means within the vicinity of a patient for reinfusion. The container further includes a lid with a nest formed on the outside surface of the lid for employing a one-handed procedure for encapsulating a blood spike. The nest stores and dispenses a blood spike cover used to encapsulate and seal the distal end of the blood spike. The one-handed procedure comprises the steps of disengaging the blood spike from a spike port of an autotransfusion system and inserting the blood spike into the nest of the container lid. Once inserted inside the nest, the cover snaps on and seals the blood spike. The user may then safely remove the covered blood spike from the nest without fear of contamination.

6 Claims, 12 Drawing Sheets

D-D

B–B

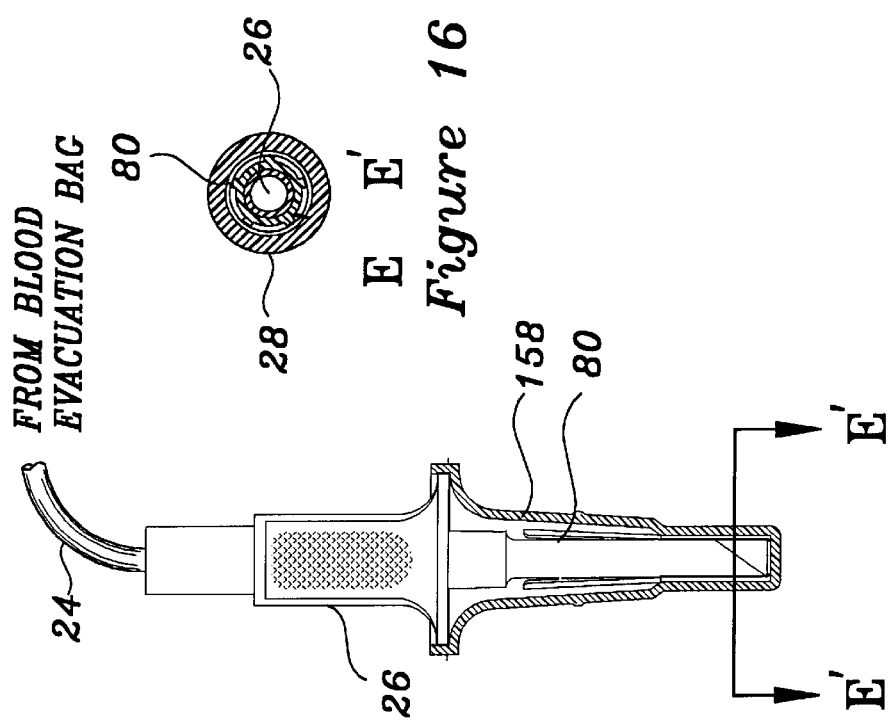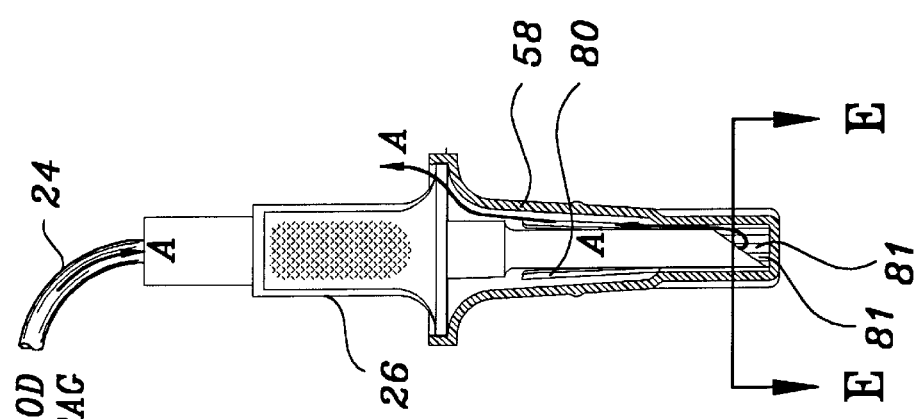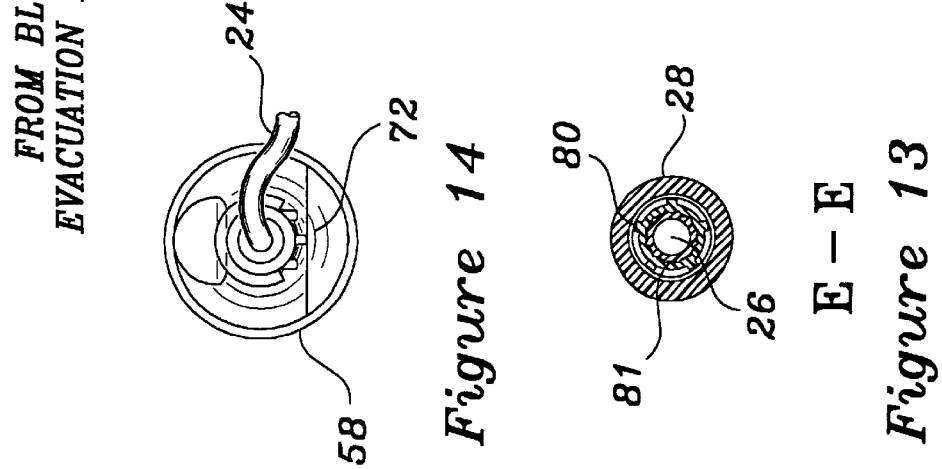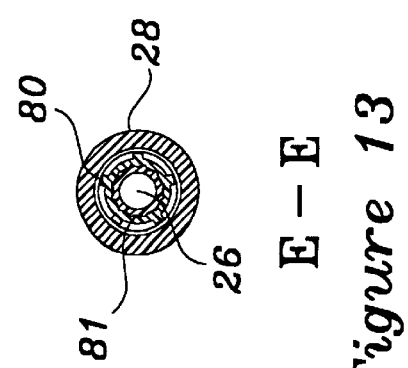

FROM CHEST DRAINAGE UNIT

TO BLOOD EVACUATION BAG

TO BLOOD EVACUATION BAG

FROM CHEST DRAINAGE UNIT

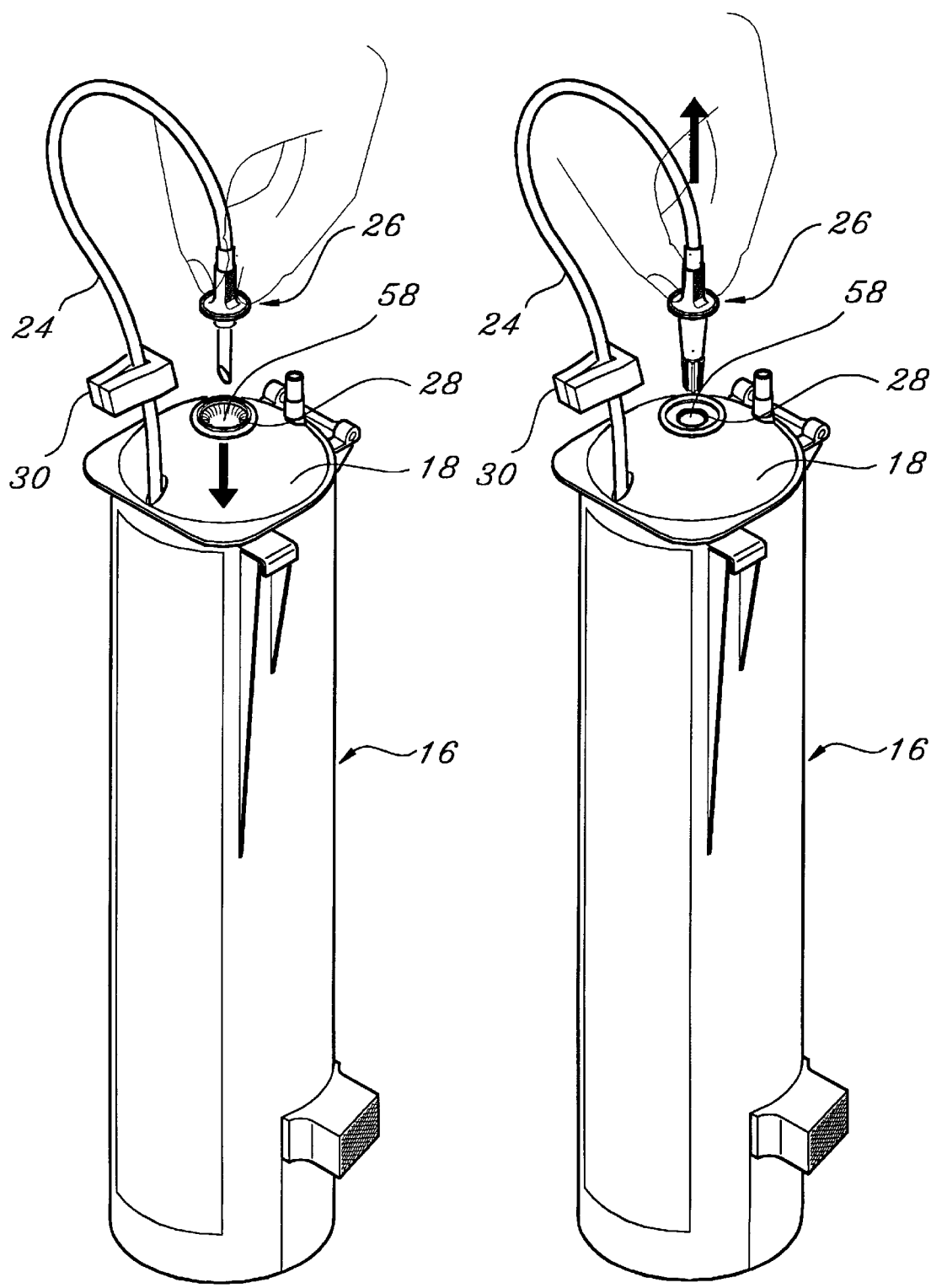
*Figure 19*    *Figure 20*

BLOOD EVACUATION CONTAINER WITH BLOOD SPIKE NESTING FEATURE

BACKGROUND OF THE INVENTION

1. Field of the Invention

The present invention generally relates to an apparatus and method for covering a connector, and particularly to an apparatus and method for disconnecting and encapsulating a connector in a fluid collection system. More specifically, the present invention relates to a blood evacuation container having a nest that houses a cover for safely encapsulating a blood spike using only a one handed procedure.

2. Prior Art

Blood evacuation apparatuses are commonly used in autotransfusion systems for the purpose of collecting and reinfusing autologous blood to a patient. Autotransfusion refers to the reinfusion of a patient's own blood, known as autologous blood. Autotransfusion is the preferred method of transfusion since the blood being reinfused is the patient's own, therefore eliminating problems over blood type incompatibility and blood carrying diseases such as hepatitis and AIDS, etc. Moreover, autologous blood is more fresh than stored blood supplied by a donor and also contains the patient's own antibodies.

One type of autotransfusion, referred to as "post-operative" autotransfusion, is the transfusion of the patient's own shed blood following surgery where drained blood is collected and reinfused into the patient. Post-operative autotransfusion is limited in use since there are strict guidelines for the kind of blood which can be reinfused. Currently, the only post-operative blood believed suitable for autotransfusion is mediastinal blood, i.e. the blood which comes from the anatomical space or cavity in the chest.

Presently, chest drainage units are commonly used in the post-operative care of patients having surgery involving the chest cavity. Chest drainage units remove fluids and air from the inside of the chest cavity using tubing connected to the patient's chest cavity which drains the fluid and air into a collection chamber of the chest drainage unit. The chest drainage unit is attached to a source of vacuum which applies suction to the tubing and draws the trapped fluid and air from the chest cavity into the collection chamber. Once collected, the blood may be evacuated from the collection chamber using an autotransfusion pump or blood evacuation bag.

The use of blood evacuation systems, and particularly blood evacuation bags, in autotransfusion is well known. For example, U.S. Pat. No. 5,201,703 to Gentelia et al. discloses an apparatus for collecting blood from a chest drainage unit and reinftision of the blood back to the patient and is incorporated herein by reference in its entirety. The '703 apparatus uses a rigid outer container that is permanently attached to a flexible inner bag in fluid flow communication with the collection chamber of a chest drainage unit. Such types of apparatuses normally employ a needle or blood spike attached to the distal end of tubing connected to the blood evacuation bag. To establish fluid flow communication between the chest drainage unit and the blood evacuation bag, a user inserts the blood spike into a spike port or self-sealing diaphragm attached to the chest drainage unit. A source of vacuum is then applied to the outer container which generates a negative pressure in the interstitial space between the container and the bag. The negative pressure inside the container draws the blood from the collection chamber and into the bag through the infusion tubing linked therebetween. Once the bag is filled with blood the entire apparatus, including the outer container and inner bag, are disconnected from the chest drainage unit and suspended from a suitable suspension means in the vicinity of a patient to reinfuse collected blood.

However, one disadvantage of the above noted blood evacuation system is that the contaminated blood spike used to establish fluid flow must be safely encapsulated after use. To prevent the transmission of disease, the Occupational Safety and Health Administration (OSHA) has issued a regulation under 29 CFR § 1920.1030 that requires blood-tainted sharp items, such as blood spikes and the like, to be encapsulated by a one-handed capping procedure by the user. The needle used in the '703 apparatus and other similar apparatuses in the art employs a twohanded procedure when encapsulating the needle after detachment from the chest drainage unit. Specifically, the user must encapsulate the needle of the '703 apparatus by holding a needle cover with one hand and the blood-tainted needle in the other hand while inserting the cover over the needle.

Accordingly, there exists a need in the art for a blood evacuation system and related method that employs a one-handed procedure for safely encapsulating a connector, such as a blood spike or needle.

OBJECTS AND SUMMARY OF THE INVENTION

A principle object of the present invention is to provide an efficient and safe means of encapsulating a connector.

Another object of the present invention to provide a one-handed procedure for encapsulating a connector.

A further object of the present invention is to provide an apparatus that includes a nesting area for storing a needle cover used to encapsulate a connector.

Another object of the present invention is to provide a secure snap fit between the connector and the cover.

These and other objects of the present invention are realized in a presently preferred embodiment thereof, described by way of example and not by way of limitation, which provides for an apparatus and method for a one-handed procedure that encapsulates the connector of a blood evacuation system prior to reinfusion. The blood evacuation system comprises a separable, flexible inner bag inside an outer rigid container for reinfusing shed blood drawn from the collection chamber of a chest drainage unit. The outer rigid container includes a suction port connected to a source of vacuum for applying a negative pressure within the interstitial space between the rigid container and the inner flexible bag which causes blood to be drawn into the bag. Once the bag is filled to a desired level, the bag is removed from the container and suspended using a suitable suspension means within the vicinity of a patient for reinfusion. The container further includes a lid with a nest formed on the outside surface of the lid for employing a one-handed procedure for encapsulating a blood spike. The nest stores a blood spike cover used to encapsulate the blood spike after use. The one-handed procedure comprises the steps of disengaging the blood spike from a spike port of an autotransfusion system and inserting the blood spike into a cover disposed inside the nest of the container lid. Once inserted inside the nest, the cover encapsulates the blood spike and snaps closed, and the user may safely remove the covered blood spike from the nest without fear of contamination.

BRIEF DESCRIPTION OF THE DRAWINGS

FIG. 12 is a partial cross-section view of the blood spike encapsulated in the spike cover illustrating the interior vented grooves and the air flow pathway taken during the purging procedure according to the present invention;

FIG. 13 is a cross-section view of the encapsulated blood spike along lines E—E shown in FIG. 12 illustrating the interior vented grooves of the spike cover;

FIG. 14 is a top section view of the encapsulated blood spike shown in FIG. 12 illustrating the vent formed between the flange and the spike cover according to the present invention;

FIG. 15 is a partial cross-section of the nested blood spike encapsulated in the spike cover showing the secondary seal between the blood spike and the spike cover according to the present invention;

FIG. 16 is a cross-section of the nested blood spike along lines E'—E' illustrated in FIG. 14;

FIGS. 19 and 20 are perspective views illustrating the one-handed procedure for encapsulating the blood spike with the spike cover using the nest according to the present invention.

DETAILED DESCRIPTION OF THE PREFERRED EMBODIMENTS

Figure 1:
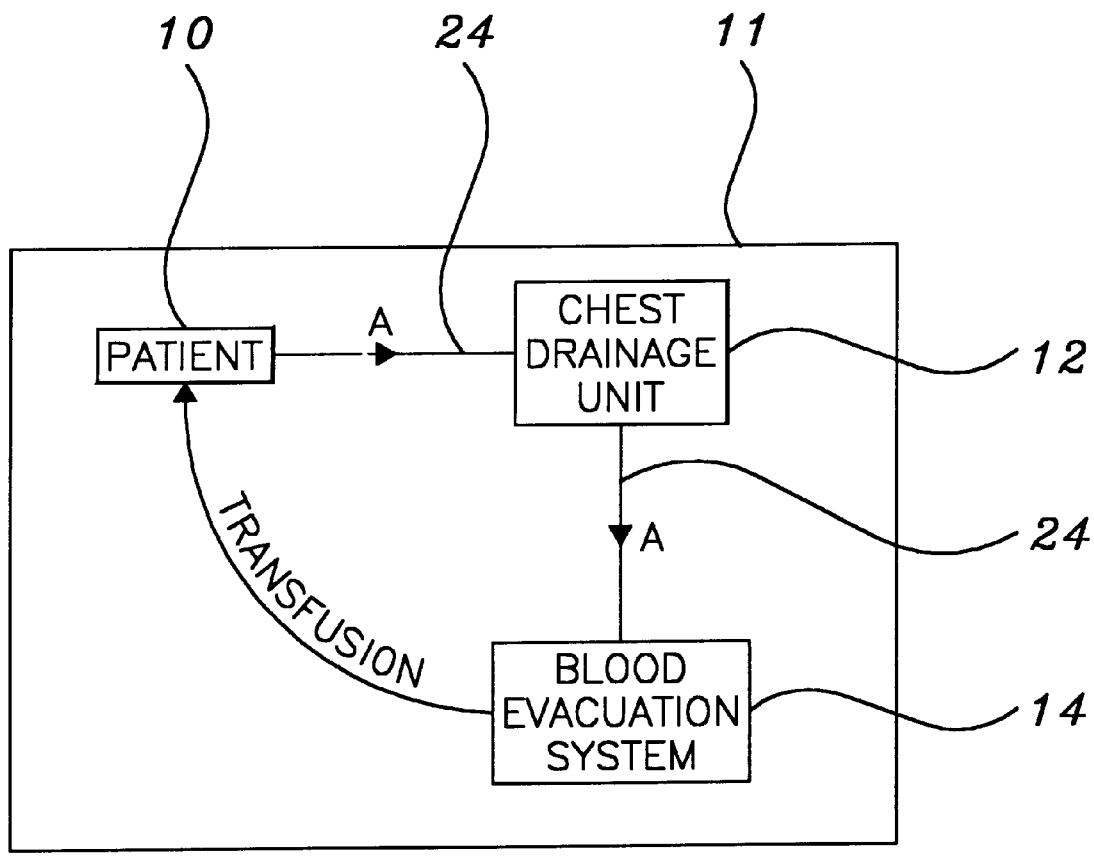
FIG. 1 is a simplified block diagram showing the blood evacuation system according to the present invention.

Referring to FIG. 1, a simplified block diagram of an autotransfusion system 11 is illustrated showing the constituent elements of system 11. The autotransfusion system 11 comprises a patient 10 in fluid flow communication with a drainage device 12 using transfer tubing 24 to maintain fluid flow communication therebetween in direction A. Preferably, the drainage device 12 according to the present invention is a chest drainage unit as disclosed in co-pending U.S. patent application Ser. No. 08/481,237, assigned to the Assignee, entitled "Spike Port with Integrated Two-Way Valve Access" and is incorporated herein by reference in its entirety. The autotransfusion system 11 further includes a blood evacuation system 14 according to the present invention that is in fluid flow communication with the drainage device 12 using the same type of transfer tubing 24 used between the patient 10 and the device 12. Preferably, the transfer tubing 24 is made of a flexible plastic material, although any flexible material suitable for transporting fluid, such as blood, is felt to fall within the scope of the present invention.

Figure 2:
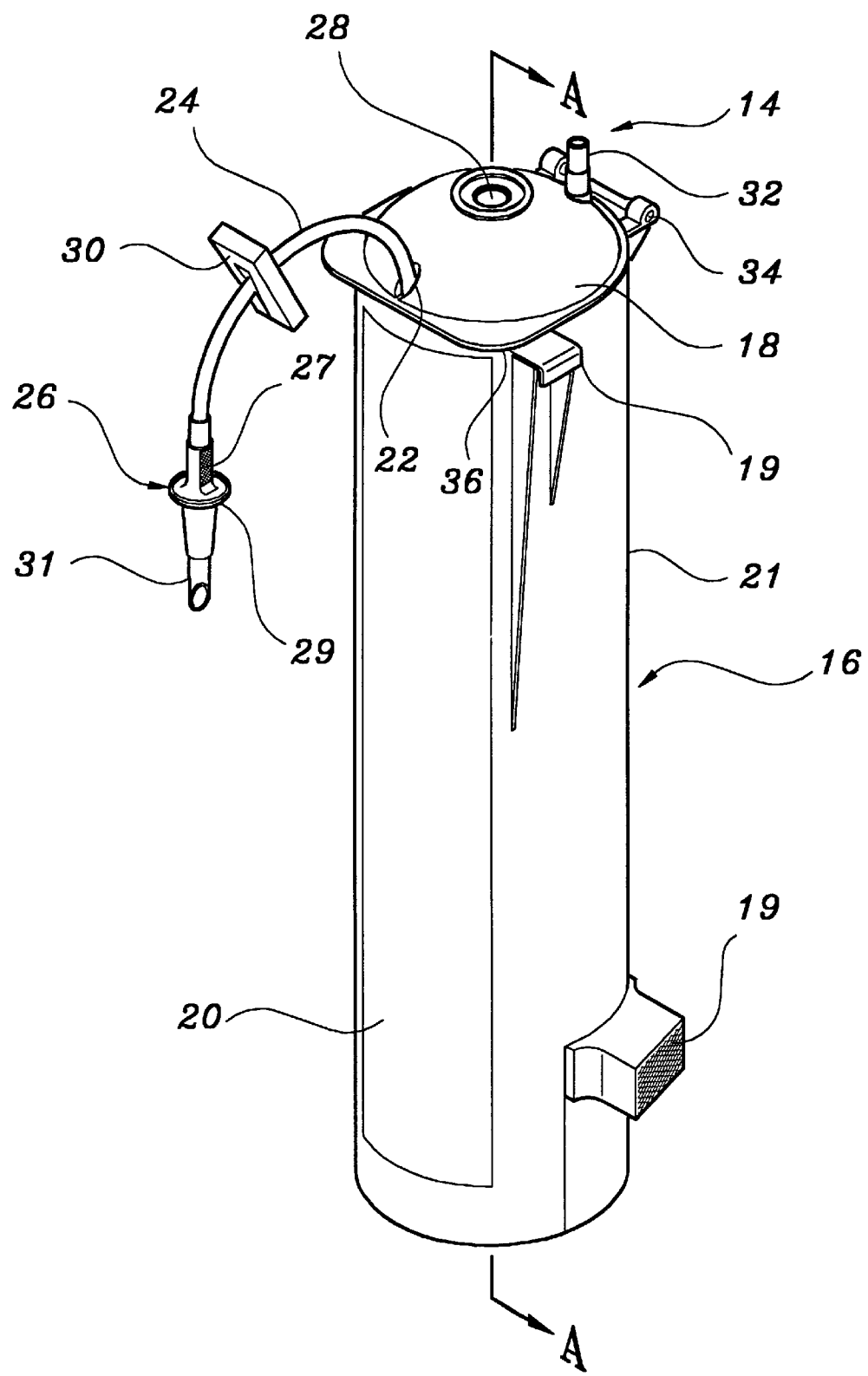
FIG. 2 is a perspective view of the rigid outer container showing the nest according to the present invention.
Figure 3:
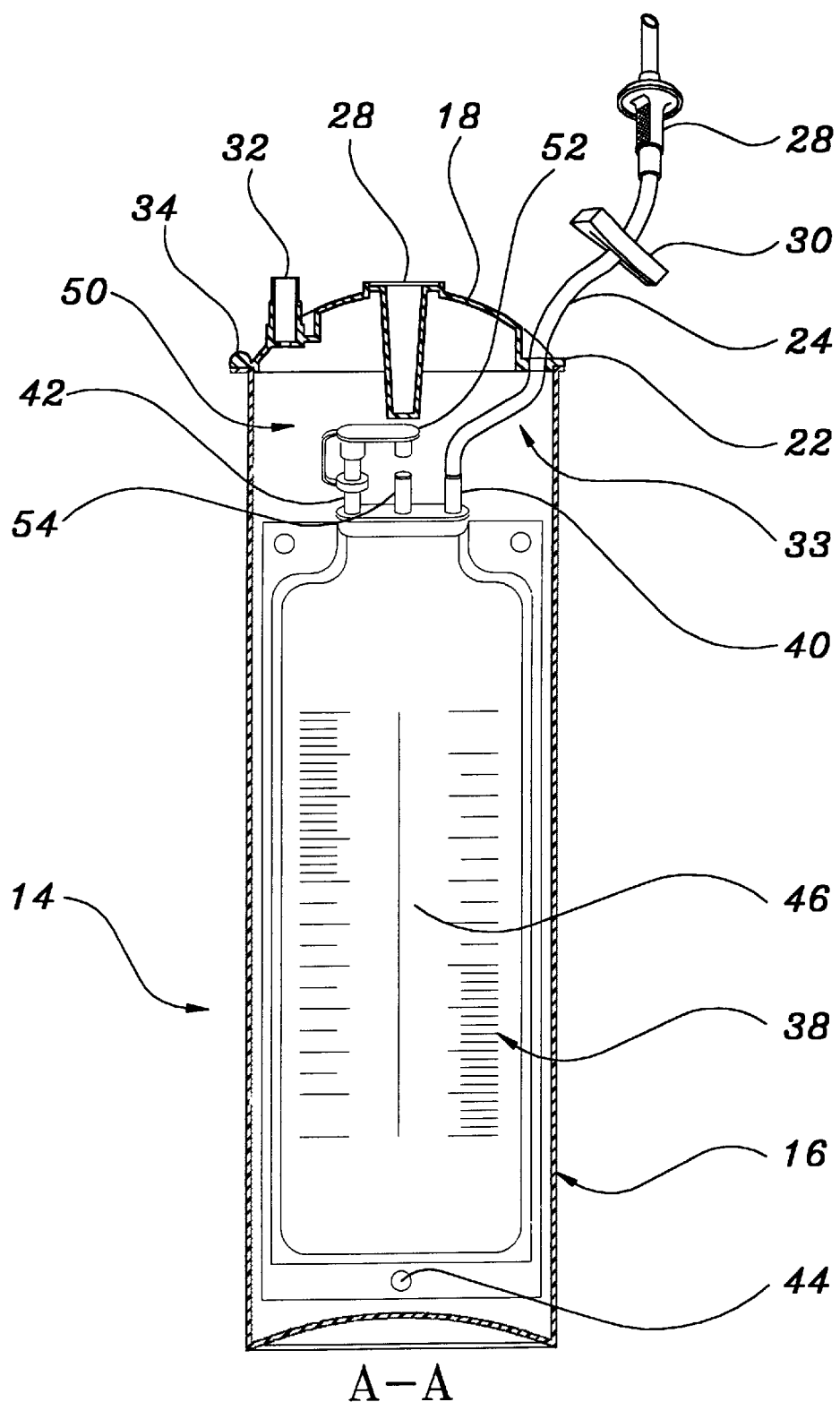
FIG. 3 is a partial cross section view of the rigid outer container and the nest along lines A—A shown in FIG. 2 according to the present invention.
Figure 4:
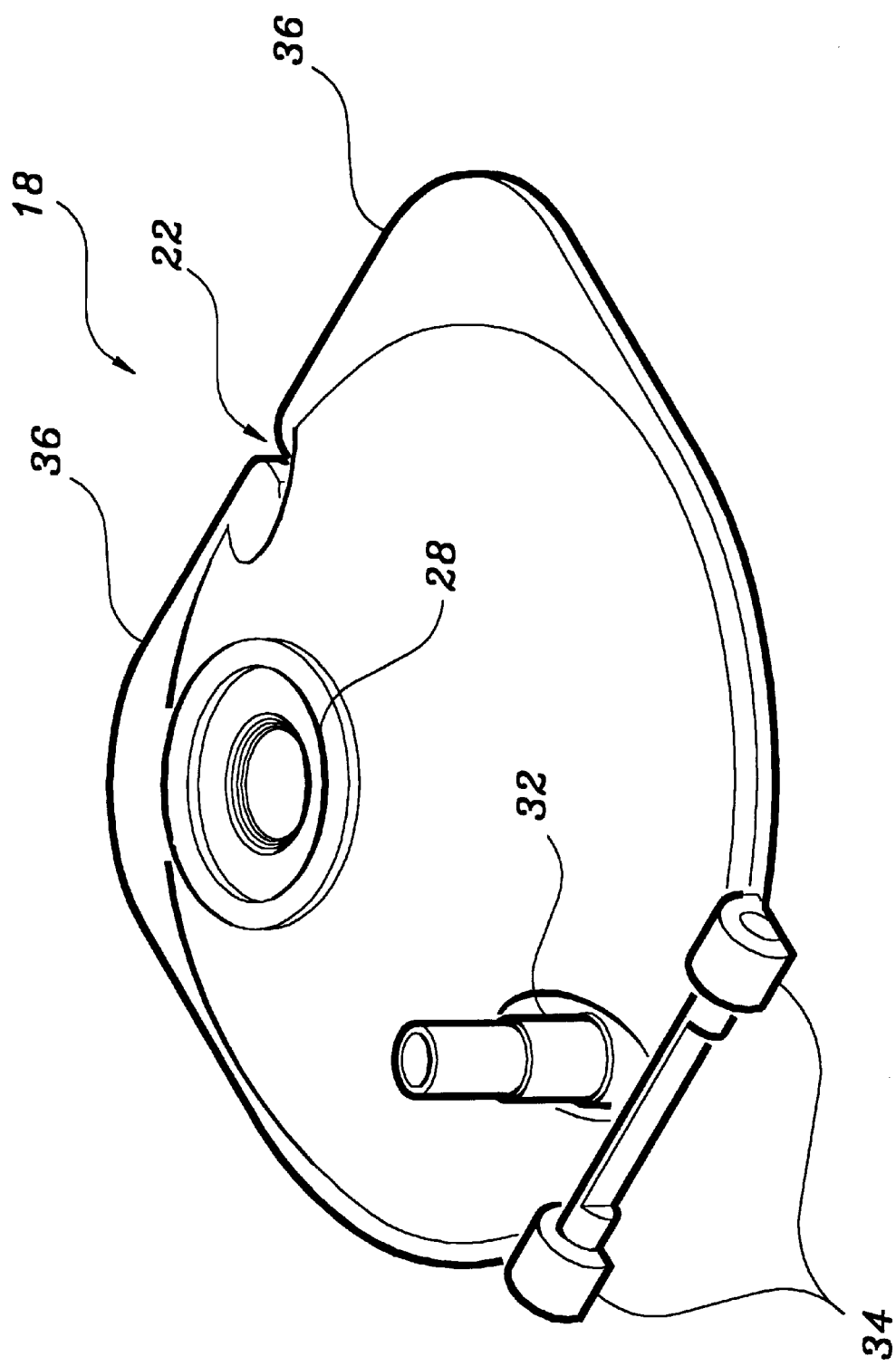
FIG. 4 is a perspective view of the canister lid shown in FIG. 2 illustrating the interior of the nest according to the present invention.

Referring to FIGS. 2–4, the blood evacuation system 14 according to the present invention is shown. The blood evacuation system 14 comprises a rigid canister 16 with a flexible blood evacuation bag 38 disposed therein. Preferably, the canister 16 has a generally tubular cross-section, although any shaped container suitable for storing fluid is felt to fall within the scope of the present invention. The canister 16 includes a lid 18 that is attached to a canister body 21 by hinges 34 which permit the lid 18 to swing freely about the hinges 34 when opening and closing the canister 16. The canister 16 also includes a labeling area 20 on the outer surface for preferably displaying instructions on the use of the blood evacuation system 14 for the user. An attachment means 19 is provided on the lower and upper portions of canister 16 for attachment to a suitable suspension means, for example an IV pole, during operation. Preferably, attachment means 19 may be a VELCRO support and corresponding VELCRO loop provided on the outer surface of canister 16 for suspending the canister 16 from a suitable suspension means.

Figure 5:
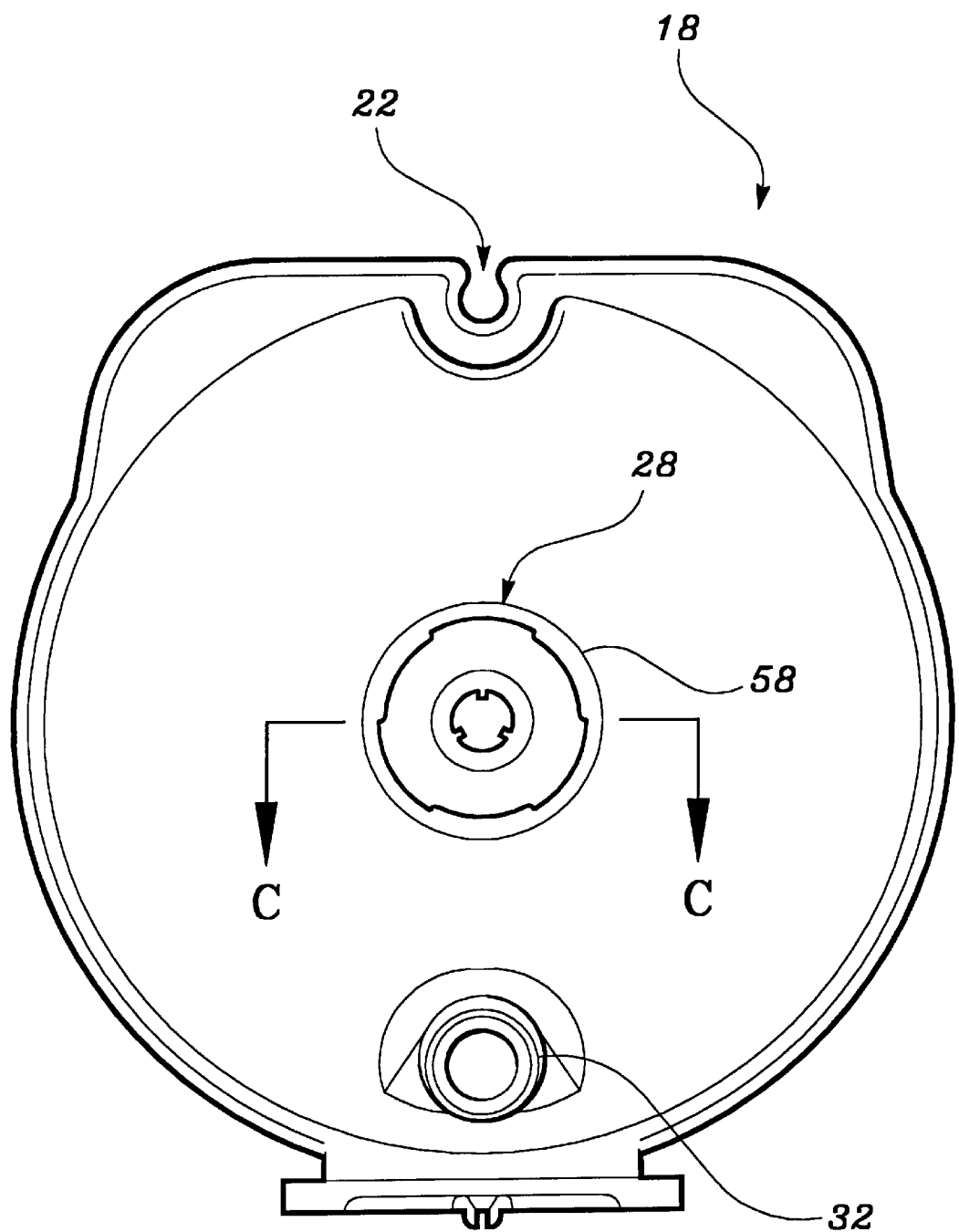
FIG. 5 is a plan view of the canister lid shown in FIG. 2 illustrating the interior of the nest according to the present invention.
Figure 7:
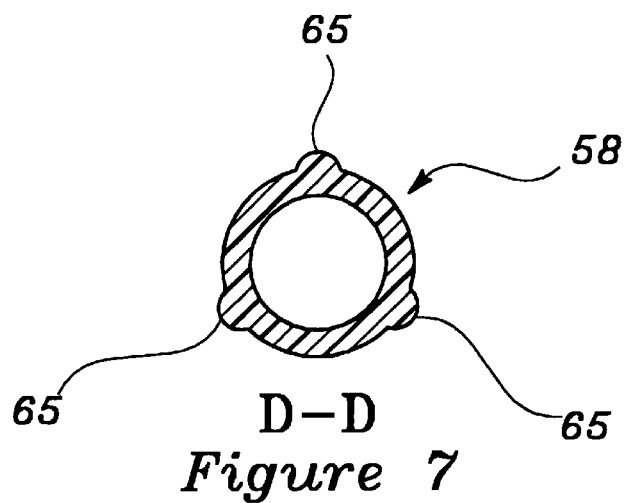
FIG. 7 is a cross-section view of the spike cover along lines D—D shown in FIG. 6 illustrating the round protrusions of the spike cover according to the present invention.

As shown in greater detail in FIGS. 4 and 5, the lid 18 of canister 16 has a dome-like shape with a suction port 32 adapted for connection to a vacuum source that in fluid flow communication with the interior space 33 (shown in FIG. 3) inside the canister 16. The lid 18 further includes a tubing groove 22 formed along the rim of lid 18 and a spike cover nest 28 formed in the middle area of lid 18 for storing a spike cover (FIG. 5) therein. The tubing groove provides an opening whereby the transfer tubing 24 attached to the blood evacuation bag 38 is inserted therethrough. Although the tubing groove 22 does not maintain a hermetic seal inside the canister 16, sufficient negative pressure is maintained inside the interstitial space 50 between the canister body 21 and the blood evacuation bag 38 to generate enough negative pressure inside the canister 16 for drawing blood into the blood evacuation bag 38 from a collection chamber (not shown) of the drainage device 12.

Referring back to FIG. 3, the blood evacuation bag 38 disposed inside the canister 16 has a plurality of ports located at the top portion of bag 38. One port, a reinfusion port 42, is initially capped using a plug 52 that prevents fluid flow and provides a site for draining collected blood from the blood evacuation bag 38 after the bag 38 is separated from canister 16 during the reinfusion procedure. Another port, an infusion port 40, is provided for attachment to transfer tubing 24 leading from the drainage device 12 for the collection of blood.

The blood evacuation bag 38 also includes an expandable interior space 46 used for the collection of shed blood drawn from the drainage device 12. As shed blood is collected inside the interior space 46, the space 46 expands until the blood evacuation bag 38 is filled to a desired level. A hole 44 formed at the bottom portion of the blood evacuation bag 38 below the interior space 46 serves as a site for suspending the bag 38 during reinfusion. A clamp 30 is also provided at transfer tubing 24 between the canister 16 and the drainage device 12 to prevent fluid flow through transfer tubing 24 when the user wishes to stop the flow of drawn blood into the blood evacuation bag 38. The blood evacuation bag 38 may be made of a flexible plastic material, although any material suitable for collecting and reinfusing fluid, like blood, is felt to fall within the scope of the present invention.

Referring back to FIGS. 4 and 5, the nest 28 of lid 18 will be discussed in greater detail. Nest 28 is formed on the outer surface of the lid 18 and is adapted to store a spike cover 58 in a snap fit connection thereto. Blood spike 26 is then inserted into the nested spike cover 58 by a user during an encapsulation procedure to be discussed in greater detail below. Nest 28 has a generally conical shape that tapers gradually inward and is configured to receive and store spike cover 58. During manufacturing, the spike cover 58 is inserted and stored inside the nest 28 in a snap fit relationship thereto, so that the cover 58 does not dislodge from the nest 28 during transportation of the blood evacuation system 14 after manufacturing.

Figure 6:
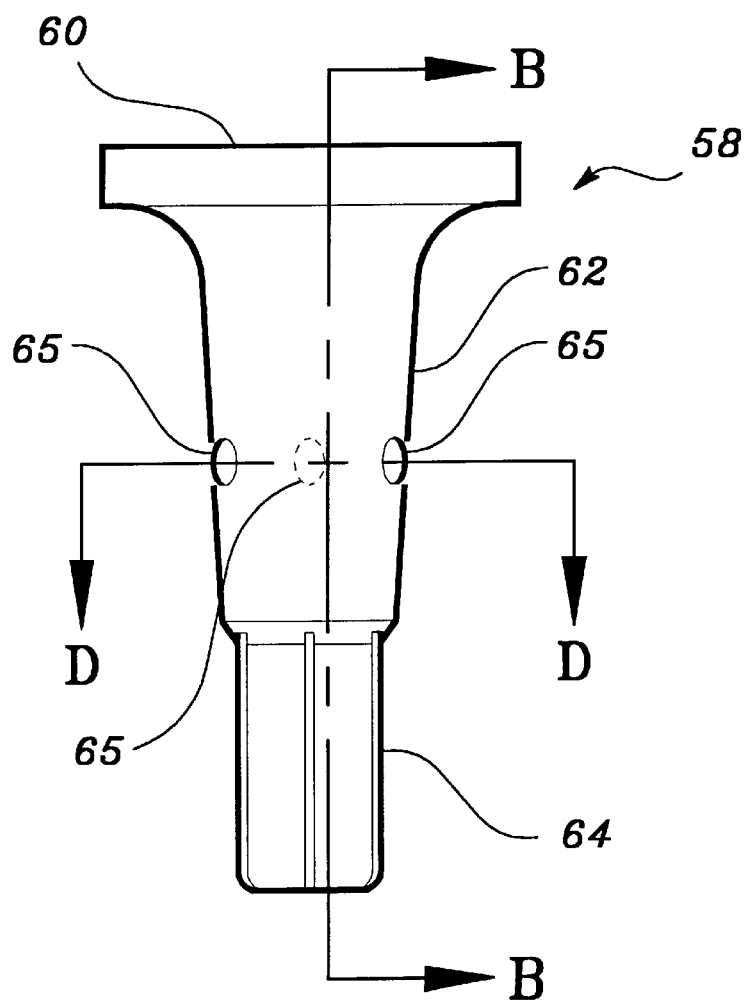
FIG. 6 is a side view of the spike cover according to the present invention.
Figure 9:
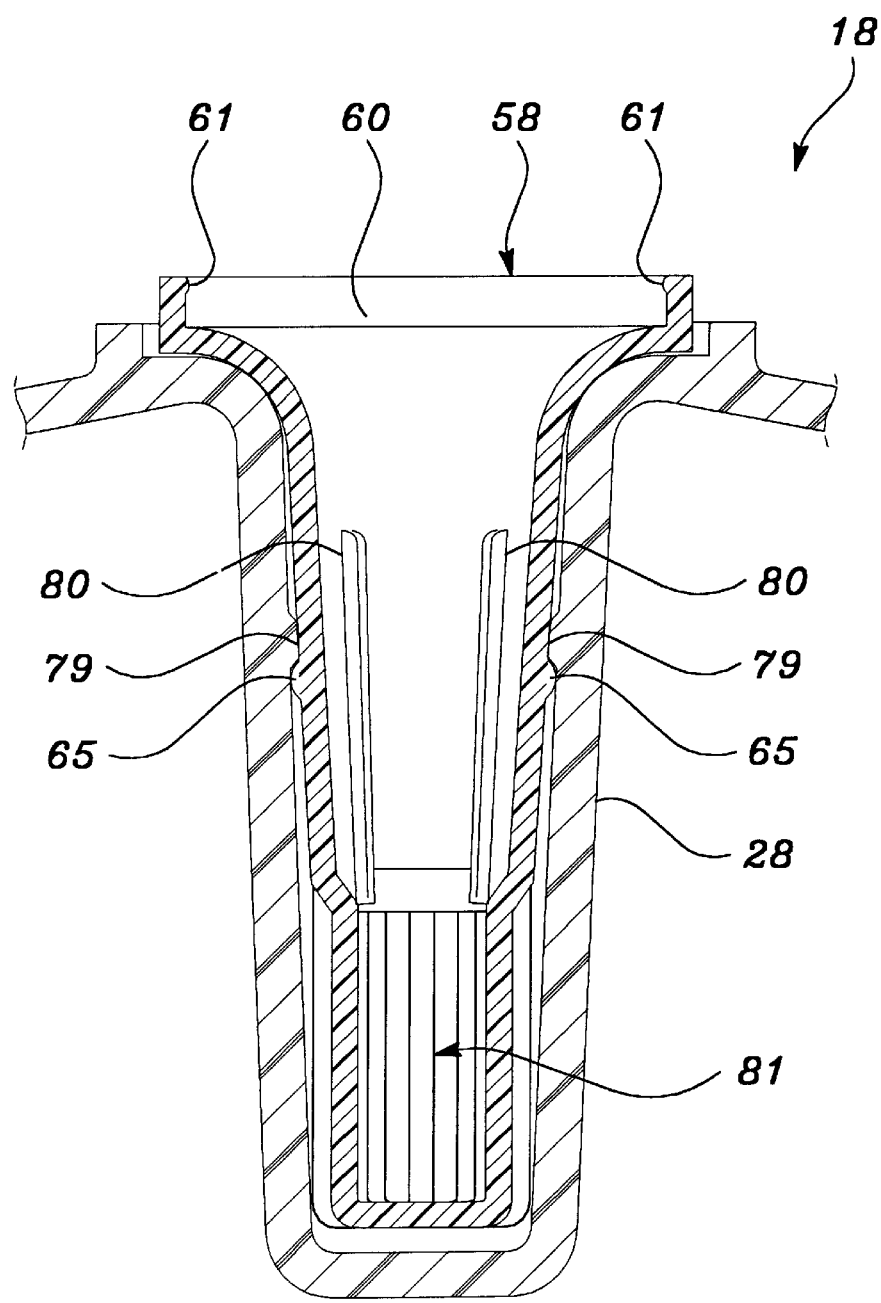
FIG. 9 is a cross-section view of the nest with the spike cover inserted therein along lines C—C shown in FIG. 5 according to the present invention.

Referring to FIG. 6, spike cover 58 has a generally frustoconical shape and includes a cover body 62 with a cover opening 60 at the proximal end of cover 58 and a ribbed portion 64 at the distal end. The middle portion of spike cover 58 has a plurality of round protrusions 65 that provide the above noted snap fit used to engage and securely store the spike cover 58 inside the nest 28. As shown in FIG. 9, the interior surface of nest 28 contains a circular ridge 79 that is adapted to engage in snap fit relationship the plurality of protrusions 65 as the cover 58 is inserted into the nest 28. The cover opening 60 includes a lip 61 that protrudes slightly inward around the inner edge of opening 60 adapted for securing the flange 29 of blood spike 26 to lip 61 of the spike cover 58 during engagement thereto. As shown in FIG. 6, blood spike 26 comprises a flange 29 interposed between a spike handle 27 at the proximal end and a pointed end 31 at the distal end of spike 26. Alternatively, circular ridge 79 may have a plurality of detents or other type of projecting member for creating the above-noted snap fit relationship with blood spike 26.

Figure 8:
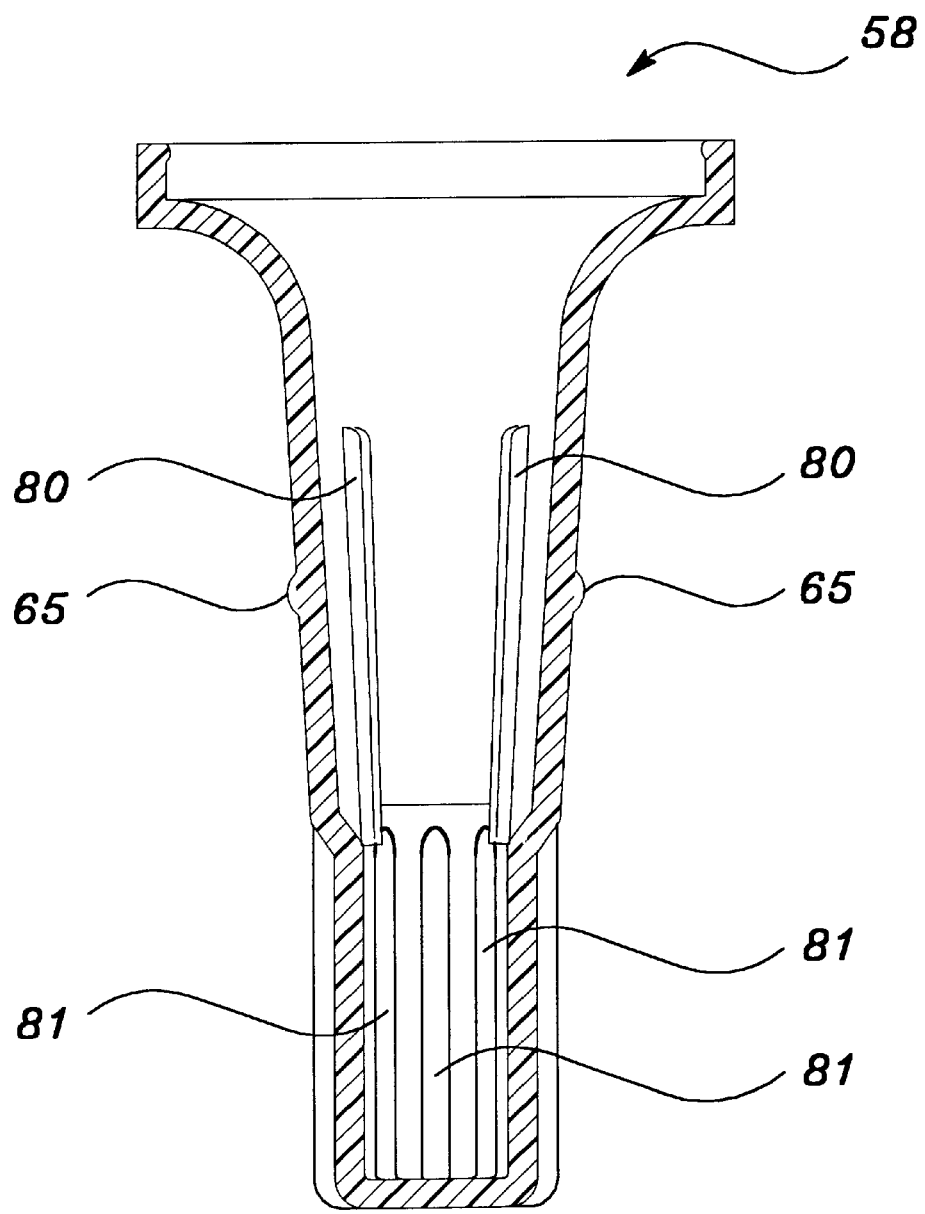
FIG. 8 is a cross-section view of the spike cover along lines B—B shown in FIG. 6 according to the present invention.

As shown in FIGS. 8 and 9, the interior surface of spike cover 58 also includes a plurality of axially extending guiding ridges 80 located along the middle portion of cover 58 that guide the pointed end 31 of the blood spike 26 downward as the user inserts the spike 26 into the cover 58. The interior surface of cover 58 further includes a plurality of axially extending venting grooves 81 at the bottom portion thereof. The venting grooves 81 allow the blood evacuation bag 38 to be purged of any air prior to reinfusion of fluids back to the patient by permitting the user to bleed the air through the encapsulated blood spike 26 after it has been engaged to the cover 58, as shall be discussed in greater detail below.

Figures 10, 11:
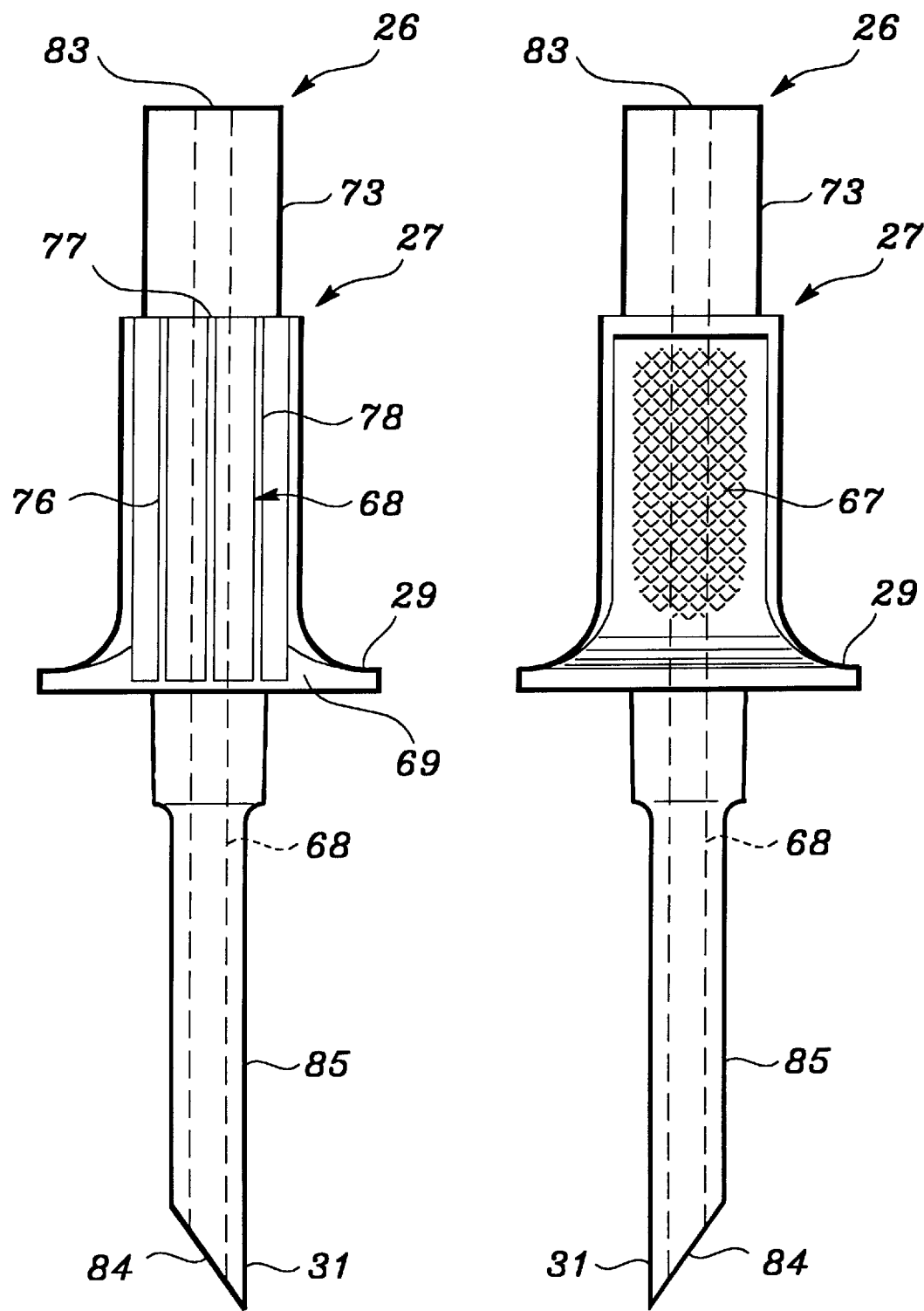
FIG. 10 is a side view of the blood spike according to the present invention.
FIG. 11 is another side view of the blood spike according to the present invention.

As shown in FIGS. 10 and 11, blood spike 26 includes a generally semi-circular shaped flange 29 interposed between a spike handle 27 at the proximal end of spike 26 and a pointed end 31 at the distal end thereof. The top of spike handle 27 forms a circular member 73 that is adapted for securely attaching transfer tubing 24 for fluid flow communication through a channel 68 formed inside the blood spike 26. The channel 68 forms a coaxial bore that extends from a first opening 83 at circular member 73 and terminates at a second opening 84 at pointed end 31 and provides fluid flow communication between the first and second openings 83 and 84. A tubular pointed member 85 is formed between the flange 29 and the pointed end 31 of the blood spike 26 and serves as a conduit for fluid that flows from the drainage device 12 into the blood evacuation bag 38 during the evacuation of fluid from device 12.

Spike handle 27 has a generally circular shape that is broken by two opposed flat gripping surfaces used for enhanced gripping between a user's thumb and forefinger. Referring to FIG. 11, one gripping surface forms a bumped surface 67 having a matrix of small bumps 75 that are adapted for better gripping by a user's thumb. In particular, bumped surface 67 has a flat shape that tapers outward at an acute angle as it meets flange 29 and provides a suitable surface for placing a user's thumb during handling of the blood spike 26. In opposed relationship to bumped surface 67 is a ridged surface 68 that forms a gripping surface comprising a plurality of alternating ridges 76, 77 and 78 and passages that extend vertically down handle 27. The two end ridges 76, 77 are equally spaced on either side of a middle ridge 78 around the circular periphery of spike handle 27. The top edges of the two end ridges 76, 77 are slightly higher than the top edge of middle ridge 78 in order to form a generally flat gripping surface for a user's forefinger along the top edges of all three ridges 76, 77, 78.

Figure 18:
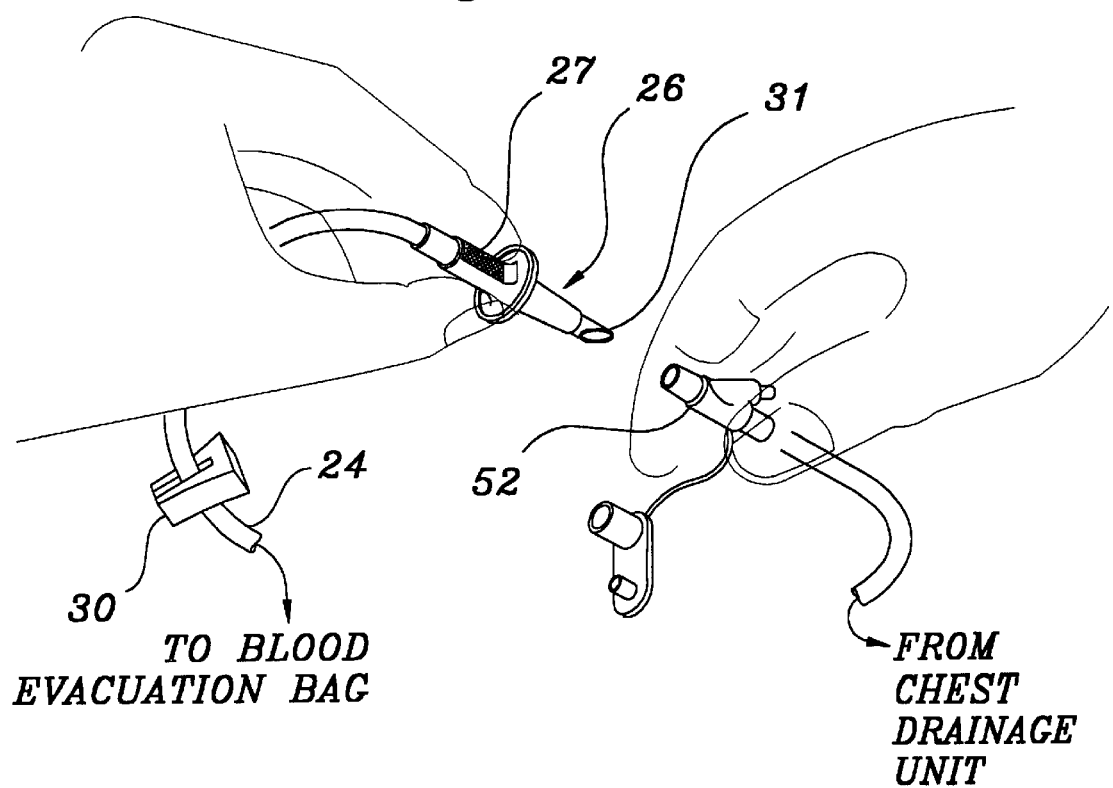

Flange 29 of blood spike 26 has a generally semi-circular shape with a flat edge 69 formed at one end of flange 29 that is flush with the ridged gripping surface 68. As illustrated in FIG. 14, flat edge 69 forms a vent 72 in combination with the lip 61 of cover 58 when the blood spike 26 is engaged to cover 58. As shall be explained in greater detail below, vent 72 permits the user to employ a method of bleeding air from the blood evacuation bag 38 after the blood spike 26 is encapsulated by the cover 58. Referring to FIGS. 12 and 13, the method of bleeding air through the venting grooves 81 of spike cover 58 when blood spike 24 has been encapsulated therein is performed using the following steps. Once the blood evacuation bag 38 is filled to a desired level the user disengages the blood spike 26 from the transfer tubing 24 leading from the Chest Drainage Unit (FIG. 18). The user then encapsulates the blood spike 26 with the cover 58 using the method explained in greater detail below and removes the blood evacuation bag 38 from the canister 16. In order to purge any air remaining in the blood evacuation bag 38, the user presses inward against the exterior surface of the blood evacuation bag 38 using his or her hands (not shown), thereby purging air from the bag 38 and into the transfer tubing 24 leading to the blood spike 26. As illustrated by air flow pathway A in FIG. 12, purged air from blood evacuation bag 38 approaches blood spike 26 and passes through channel 68 of spike 26 where the purged air is forced into the bottom cavity 82 formed between the pointed end 31 and the interior surface of cover 58. Purged air then passes between the venting grooves 81 as it rises between blood spike 26 and cover 58 and is released through vent 72 (FIG. 14) until a sufficient amount of purged air is bled from the blood evacuation bag 38, thereby completing the purging procedure.

Referring to FIGS. 15 and 16, an alternative embodiment, spike cover 158, is shown. Spike cover 158 has the same configuration as preferred cover 58, but differs in that cover 158 lacks the venting grooves 81 that permit purging of air from blood evacuation bag 38. Instead, spike cover 158 forms a seal around blood spike 26 that prevents fluid flow therefrom.

Figure 17:
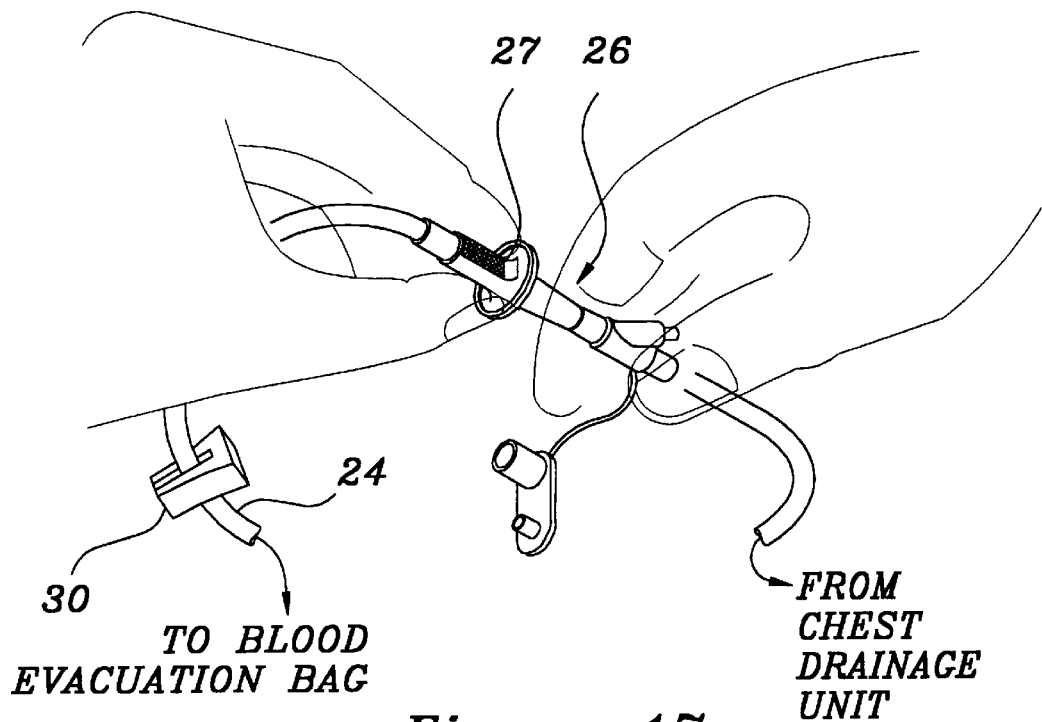
FIGS. 17 and 18 are perspective views illustrating how the blood spike is disengaged from the spike port according to the present invention.

Referring to FIG. 17, the method of connecting the blood spike 26 to the drainage device 12 will be briefly discussed. In establishing fluid flow communication between the blood evacuation bag 38 and the drainage device 12, a user engages the blood spike 26 to the spike port 52. Preferably, the spike port 52 according to the present invention is a spike port as disclosed in co-pending U.S. patent application Ser. No. 08/481,237, assigned to the Assignee, entitled "Spike Port with Integrated Two-Way Valve Access" and is incorporated herein by reference in its entirety, although any suitable port or self-sealing diaphragm is felt to fall within the scope of the present invention. Prior to engaging the spike port 52, a dust cover (not shown) that maintains a sterile barrier around the blood spike 26 during storage and transportation after manufacturing is removed. After the user engages the blood spike 26 to the spike port 52, the clamp 30 that occludes the transfer tubing 24 is released and the user applies a source of vacuum to the suction port 32. When vacuum is applied, negative pressure builds inside an interstitial space 50 between the canister 16 and the blood evacuation bag 38. As negative pressure increases inside the interstitial space 50, blood from the drainage device 12 is drawn through transfer tubing 24 and fills the interior space 46 of the blood evacuation bag 38.

Once the blood evacuation bag 38 is filled to a desired level, reinfuision of the blood may take place. The reinfusion procedure begins by the user turning off the source of vacuum and applying the clamp 30 to the transfer tubing 24, thereby preventing fluid flow therethrough from the drainage device 12.

Referring to FIG. 18, the method for disengaging the blood spike 26 from the spike port 52 will be discussed. To disengage the blood spike 26, the user employs a two-handed procedure by grasping the spike handle 27 of the blood spike 26 with one hand and the spike port 52 with the other hand. The user then disengages the blood spike 26 by employing a twist and pull motion away from the spike port 52, thereby releasing the blood spike 26.

Referring to FIGS. 19 and 20, the one-handed method of encapsulating the blood spike 26 after removal from the spike port 52 according to the present invention will be discussed. As illustrated in the drawings, the user grasps the spike handle 27 with one hand and inserts the pointed end 31 of the blood spike 26 into the nest 28. The nest 28 stores the spike cover 58 which is adapted to securely attach to the blood spike 26 when the user inserts the pointed end 31 of the spike 26 into the spike cover 58 disposed therein. Upon insertion, the flange 29 of the blood spike 26 engages the lip 61 of the spike cover 58 in a snap-on relationship thereto which effectively seals the distal end of the blood spike 26, thereby encapsulating the pointed end 31 of spike 36. Once the blood spike 26 is sealed, contamination from the pointed end 31 is prevented and the one-handed encapsulation procedure is completed.

After encapsulating the blood spike 26, the lid 18 is opened and the blood evacuation bag 38 is removed from the canister 16 and suspended in the vicinity of the patient using suitable suspension means, i.e., an IV pole. Once suspended, the user establishes fluid flow communication between the patient 10 and the blood evacuation bag 38 by removing the plug 48 from the reinfusion port 42 and attaching the transfer tubing 24 connected to the patient 10 to the port 42.

While reinfusion is occurring, the user may continue evacuating blood from the drainage device 12 by inserting another blood evacuation bag 38 into the canister 16 and reestablishing fluid flow communication between the bag 38 and the drainage device 12 as noted above. In this manner, "batch" autotransfusion takes place by simply replacing the blood evacuation bag 38 inside the canister 16 every time a bag 38 is removed for reinfusion.

It should be understood from the foregoing that, while particular embodiments of the invention have been illustrated and described, various modifications can be made thereto without departing from the spirit and scope of the invention. Therefore, it is not intended that the invention be limited by the specification; instead, the scope of the present invention is intended to be limited only by the appended claims.

I claim:

1. An evacuation system for the collection of fluid comprising:
   a container including a lid, said container having a nest formed on an outside surface of said container, said nest storing a cover, and
   a bag disposable inside said container, said bag including a port for attachment to a proximal end of tubing, a distal end of said tubing having a connector for connection to the source of fluid to be collected in said bag,
   wherein said cover is adapted to engage and encapsulate said connector when said connector is inserted into said nest.

2. The evacuation system according to claim 1, wherein said nest stores and dispenses said cover when a user inserts said connector into said nest.

3. The evacuation system according to claim 1, wherein said lid forms part of said outside surface of said container.

4. The evacuation system according to claim 3, wherein said nest is formed inside said lid.

5. The evacuation system according to claim 1, wherein said cover snaps securely over said connector to deter disengagement of said cover.

6. The evacuation system according to claim 1 wherein said cover has a distal end, said distal end providing a secondary clamp that seals a distal end of a blood spike.

* * * * *

UNITED STATES PATENT AND TRADEMARK OFFICE
CERTIFICATE OF CORRECTION

PATENT NO.   : 6,183,453 B1
DATED        : February 6, 2001
INVENTOR(S)  : David Rork Swisher It is certified that error appears in the above-identified patent and that said Letters Patent is hereby corrected as shown below:

Column 1,
Line 3, please add the following text:
-- CROSS-REFERENCE TO RELATED APPLICATIONS:
 The present application claims priority under 35 U.S.C 119(e) to U.S., Provisional Patent Application serial number 60/066,214 filed on November 20, 1997. --

Signed and Sealed this

Twenty-ninth Day of July, 2003

JAMES E. ROGAN
*Director of the United States Patent and Trademark Office*